United States Patent
Sakata et al.

(10) Patent No.: US 6,746,663 B2
(45) Date of Patent: Jun. 8, 2004

(54) PORPHYRIN COMPOUNDS

(75) Inventors: Isao Sakata, Okayama (JP); Susumu Nakajima, Asahikawa (JP); Yoshinori Nakae, Okayama (JP)

(73) Assignee: Photochemical Co., Ltd., Okayama (JP)

( * ) Notice: Subject to any disclaimer, the term of this patent is extended or adjusted under 35 U.S.C. 154(b) by 259 days.

(21) Appl. No.: 09/889,698

(22) PCT Filed: Nov. 29, 2000

(86) PCT No.: PCT/JP00/08386

§ 371 (c)(1),
(2), (4) Date: Jul. 20, 2001

(87) PCT Pub. No.: WO01/40234

PCT Pub. Date: Jun. 7, 2001

(65) Prior Publication Data

US 2003/0017112 A1 Jan. 23, 2003

(30) Foreign Application Priority Data

Nov. 30, 1999 (JP) ............................................. 11/339330

(51) Int. Cl.[7] ............................ A61B 10/00; A61B 5/00; A61B 8/00

(52) U.S. Cl. ......................... 424/9.61; 424/9.6; 424/9.1; 424/1.11; 424/1.65; 540/145

(58) Field of Search ................................ 424/1.11, 1.65, 424/9.1, 9.3, 9.36, 9.362, 9.4, 9.5, 9.6, 9.61, 9.7, 9.8; 534/7, 10–16; 540/145

(56) References Cited

U.S. PATENT DOCUMENTS 6,063,777 A * 5/2000 Hikida et al. ................ 514/183

FOREIGN PATENT DOCUMENTS

| JP | 4-59779 | 2/1992 |
| JP | 5-97857 | 4/1993 |
| JP | 9-124652 | 5/1997 |
| JP | 09124652 A * | 5/1997 |

* cited by examiner

*Primary Examiner*—Dameron L. Jones
(74) *Attorney, Agent, or Firm*—Crowell & Moring LLP

(57) ABSTRACT

The present invention provides the porphyrin compound which is used for photodynamic diagnosis and/or treatment for animals, and the photodynamic diagnostic and/or therapeutic agent for animals.

6 Claims, 2 Drawing Sheets

PORPHYRIN COMPOUNDS

TECHNICAL FIELD

The present invention relates to a porphyrin compound or a pharmaceutically acceptable salt thereof used for photodynamic diagnosis and/or treatment of animals. The present invention also relates to a photodynamic diagnostic and/or therapeutic agent comprising the porphyrin compound or a pharmaceutically acceptable salt thereof, which is used for photodynamic diagnosis and/or treatment, especially, of tumor in animals.

BACKGROUND ART

As a new method of treatment for cancer, photodynamic diagnosis and therapy (PDT: Photodynamic Therapy) has stepped into the limelight. It is a method in which a certain type of porphyrin derivatives is administered to a subject by, for example, intravenous injection to retain the porphyrin derivative in the target cancerous tissues in the subject, followed by laser irradiation to cause selective destruction of the cancerous tissues. The therapy utilizes the two properties of a porphyrin derivative, i.e., selectivity for cancerous tissues and photosensitivity.

The only porphyrin derivative currently used in PDT is porphymer sodium. Porphymer sodium is a mixture compound of 2- to 6-polymer comprising an ether and/or ester of hematoporphyrin derivative. Porphymer sodium is known to cause temporary photosensitivity as an undesirable side effect when administered to human body, and further, selective distribution to cancerous tissues is not sufficient for practical use, and therefore the problem of accumulation in normal tissues is confirmed.

Under the circumstances, a patient treated with porphymer sodium is required to stay in the dark for a long period of time until porphymer sodium is completely excreted from the body so that normal cells are not damaged by the photosensitizing action of porphymer sodium accumulated in normal tissues. However, since porphymer sodium shows a slow excretion rate from normal tissues, it sometimes causes photosensitivity to last for more than six weeks.

In addition, PDT using porphymer sodium has a problem with transmission of the light irradiated by laser through tissues. That is, porphymer sodium has a longest wavelength absorption end at 630 nm and a molar absorption coefficient is as small as 3,000. Since there are many components present in a living body which prevent the transmission of light, such as oxyhemoglobin and water, the light with wavelength of 630 nm exhibits a poor transmission through tissues, which cannot sufficiently reach to deep sites, thus, PDT using porphymer sodium is only intended for cancers developing in the surface layers of 5 to 10 mm depth. The wavelength which is least damaging by the light absorption to the components in a living body is in a range of 650 to 750 nm, therefore, photosensitizers for PDT having the longest wavelength absorption end within such range are most desirable.

Laser devices themselves also have problems. Dye lasers, which are most commonly used at present, have a poor stability in performance and therefore are difficult to handle in practical use. On the other hand, titanium-sapphire lasers enable to facilitate the practice of PDT considerably. However, these types of lasers are limited in the excitable wavelength to not less than 670 nm and not more than 600 nm, and therefore are not applicable to porphymer sodium which has an absorption wavelength of near 630 nm.

Recently, semiconductor lasers (670 nm), which are applicable to compounds exhibiting an absorption near 670 nm, have been developed, and quite recently OPO-YAG laser has been developed, which made it possible to cover almost all visible wavelengths.

As mentioned above, photosensitizers currently used for PDT have various defects and therefore development of new agents without such defects is strongly desired. In an attempt to overcome those problems, a prophyrin compound which is a single compound and exhibits its adsorption in a longer wavelength region (650–800 nm) has been proposed as a second generation agent for PDT.

Examples of such second generation agent includes amino-levulinic acid (ALA) which is a protoporphyrin precursor; asparthyl-chlorin e6 (Np e6) which is a chlorin derivative; benzoporphyrin derivative (BPD) and methatetrahydroxyphenylchlorin (m-THPC), both of which are new type of chlorin derivatives obtained by the structural conversion from hemoglobin-derived porphyrins.

In addition, the present inventors proposed chlorin derivatives and the analogues thereof, e.g., an alkoxyiminochlonyl aspartic acid derivative (Japanese Patent Application Laid-open Nos. 5-97857 and 9-124652), confirming that these compounds are useful as photosensitizers for PDT.

On the contrary, in mammals' case, suffering from cancer has been a great problem not only in human beings but in animals, especially, in pet animals which are breeding in a house. For treating the cancer of these pet animals, same treatments for human being such as administering anticancer agent or radiotherapy have been performed. Under these circumstances, the present inventors have studied to develop the effective therapeutic methods for treatment of cancer of pet animals and confirmed that among the alkoxyiminochlonyl aspartic acid derivatives, ethoxyiminochlonyl aspartic acid derivatives are useful as photosensitizers for PDT in animals.

Therefore, it is an object of the present invention to provide a porphyrin compound or a pharmaceutically acceptable salt thereof used for photodynamic diagnosis and/or treatment of animal.

Furthermore, it is other object of the present invention to provide a photodynamic diagnostic agent and/or therapeutic agent comprising the porphyrin compound or a pharmaceutically acceptable salt thereof, especially for diagnosis and/or treatment of tumor in animals.

DISCLOSURE OF THE INVENTION

To solve the above-mentioned objects, one aspect of the present invention provides a porphyrin compound represented by the following formula (I):

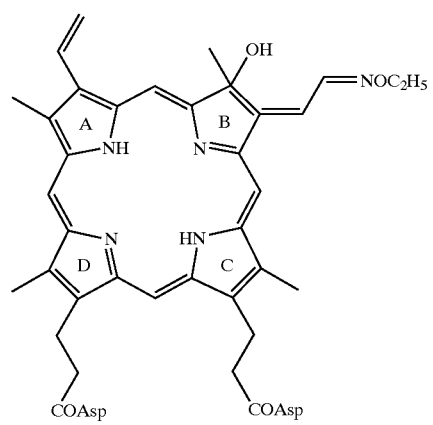

wherein Asp represents a residue of aspartic acid, or a pharmaceutically acceptable salt thereof, used for photodynamic diagnosis and/or treatment of animals.

Another aspect of the present invention provides a porphyrin compound represented by the following formula (II):

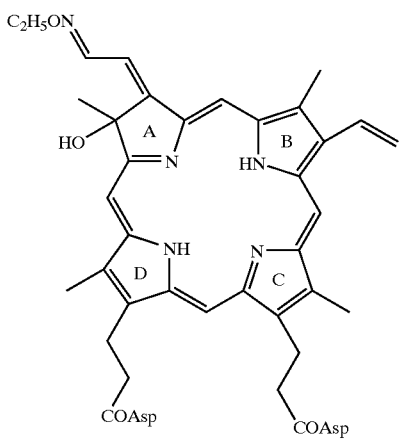

(II)

wherein Asp represents a residue of aspartic acid, or a pharmaceutically acceptable salt thereof, used for photodynamic diagnosis and/or treatment of animals.

Still another aspect of the present invention provides a photosensitizer for the photodynamic diagnosis and/or treatment containing the porphyrin compound represented by formula (I) or (II) as well as a mixture thereof, or a pharmaceutically acceptable salt thereof.

More specific embodiment of the present invention, it is provided a photosensitizer for the photodynamic diagnosis and/or treatment of tumor of animals containing the porphyrin compound represented by formula (I) or (II), or a pharmaceutically acceptable salt thereof as an active ingredient.

BEST MODE FOR CARRYING OUT THE INVENTION

Figure 1:
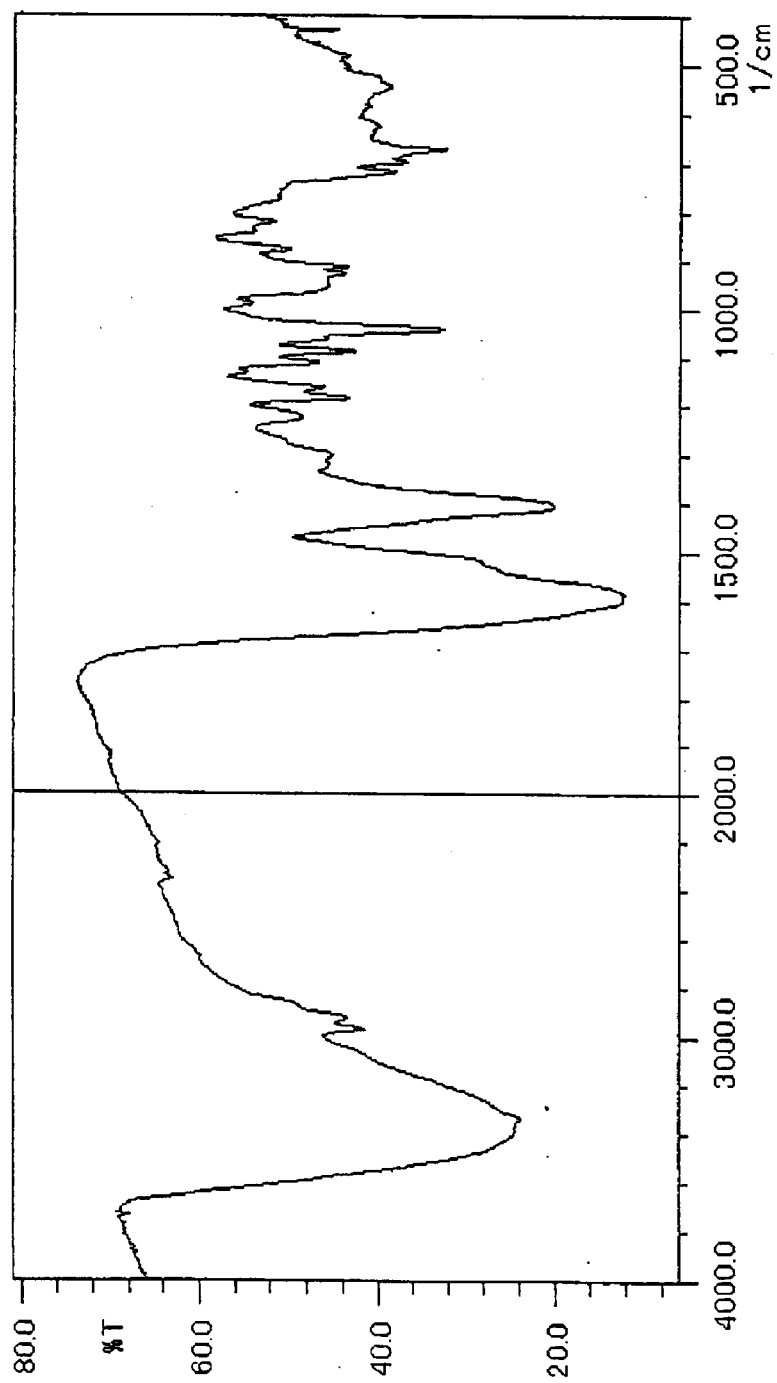
FIG. 1 shows an infrared absorption spectrum of sodium salt of the porphyrin compound of the formula (I) (NOEt-P-Asp).

The porphyrin compound of the present invention represented by formula (I) or (II) is a single component, Is stable, and has a higher excretion rate from normal tissues. Therefore, it is characterized that the porphyrin compounds of formula (I) or (II) has a reduced phototoxicity while retaining a good accumulability to cancerous tissues and, furthermore, allows the use of titanium-sapphire laser (wavelength of not less than 670 nm and not more than 600 nm) and a semiconductor laser (wavelength of 670 nm).

Furthermore, when the porphyrin compound of formula (I) was examined by albumin test and dancyl methionine test, in which one of the present inventors has found a certain rule, it was confirmed that the compound of formula (I) shows an excellent transferability to cancerous tissues and a strong photosensitivity.

Albumin test is a test method for evaluating the affinity to cancerous tissues, in which a chlorin derivative is examined on the change in ultraviolet (UV) absorption spectrum in a mixture form with albumine, and dancyl methionine test is also a convenient test method for evaluating the strength of the photoreactivity by thin layer chromatography (TLC) or high performance liquid chromatography (HPLC) (see Japanese Patent Application Laid-open No. 5-97857).

The porphyrin compounds represented by formula (I) or (II) of the present invention can be prepared by the method as mentioned below.

That is, the compound can be prepared by a method comprising Step (a) in which a protoporphyrin dimethyl ester (hereinafter referred to as "PP-Me"), as starting compound, is converted into a chlorin derivative having an aldehyde group therein; Step (b) in which the aldehyde group of the chlorin derivative thus obtained is converted to O-ethylimino group by condensation with a O-ethylhydroxylamine; and Step (c) in which the compound thus obtained is further introduced with aspartic acid via an amide bond. It is not essential to conduct the reactions in the order of (b) then (c), that is, compound of the present invention can be produced in good yield in the case the compound is condensed with aspartic acid to form the amide bond as in Step (c), and then, the aldehyde group of the compound thus obtained is converted to O-ethylimino group by condensation with a O-ethylhydroxylamine as in Step (b).

Each of the steps is explained in more detail in the following.

Step (a) for conversion of the starting compound into a chlorin derivative can be conducted according to any of the conventional methods, such as methods disclosed in J. E. Falk: "Porphyrins and metalloporphyrins" published by Elsevier in 1975: D. Dolphin: "The Porphyrins" published by Academic Press in 1978 and so on.

That is, in step (a), PP-Me is subjected to a photochemical reaction treatment to give 7-hydroxy-8-oxoethylidene-protoporphyrin dimethylester (hereinafter referred to as "P-Me(I)") and 2-hydroxy-3-oxoethylidene-protoporphyrin dimethylester (hereinafter referred to as "P-Me(II)") in a mixture form. The later compound, i.e. P-Me(II), is a position isomer of P-Me(I) with respect to the side-chained substituent in the A and B rings of four tetrahydropyrrole rings. From the mixture thus obtained, each of P-Me(I) and P-Me(II) was isolated and purified by means of silica gel column chromatography or recrystallization using a suitable solvent. A mixture of P-Me(I) and P-Me(II) can be used for next step (b) without isolation.

Next, in step (b), the aldehyde group of P-Me(I), which is isolated and purified in step (a), is converted to O-ethylimino group by condensation reaction with O-ethylhydroxylamine hydrochloride. This reaction can be conducted according to a conventional procedure as disclosed in "Condensation reaction between hydroxylamine and an aldehyde compound" in Ippan Yuki Kagaku Jikken Sho (Text for General Organic Chemical Experiments).

For example, the reaction may be conducted in suitable inert solvent in the presence of condensation reagent such as inorganic or organic base. Inorganic base may include alkali hydroxide or alkali metal carbonate, and organic base may include pyridine or piperidine. The reaction can preferably be carried in pyridine or piperidine using as a reaction solvent and as condensation reagent.

Accordingly, 7-hydroxy-8-ethoxyiminoethylidene-protoporphyrin dimethyl ester (hereinafter referred to as "NOEt-P-Me(I)") is converted from P-Me(I), and P-Me(II), which is a position isomer of P-Me(I), is also converted to 2-hydroxy-3-ethoxyiminoethyliden-protoporphyrin dimethyl ester (hereinafter referred to as "NOEt-P-Me(II)") in the same manner.

Thus obtained NOEt-P-Me(I) is subjected to step (c). That is, NOEt-P-Me(I) is hydrolyzed with an alkali in a conventional manner and then amidated with aspartic acid methyl ester to obtain aspartic acid substituted porphyrin.

This reaction may be conducted by a conventional procedure as disclosed in Izumiya et al.,: *"Peptide gosei no kiso to jikken* (*Basis and Experiments of Peptide synthesis*)", published by Maruzen in 1985, and especially a procedure as disclosed in Japanese Patent Application Laid-open Nos. 64-61481, 2-138280, 4-59779, 5-97857 or 9-124652, or Japanese Patent Publication No. 7-25763 are preferred.

By this reaction, aspartic acid residue is introduced in the side chain of the porphyrin compound, and the reaction may occur between carboxyl group at the side chain of porphyrin compound and amino group of aspartic acid. Therefore, it should be considered in the reaction to convert the carboxyl group at the side chain of porphyrin compound and/or amino group of aspartic acid to reactive substituent by conventional manner, or to protect functioning group not preferable to participate in both groups.

The reaction may be accelerated in suitable solvent using reaction accelerator such as dehydration agent and deoxidation agent which examples are dicyclohexylcarbodiimide (DCC) and water soluble carbodiimide (WSC).

According to above reaction, NOEt-P-Me(I) for example, is amidated with aspartic acid dimethylester after alkali hydrolysis, and then derived to 7-hydroxy-8-ethoxyiminoethiliden-protoporphyrin [hereinafter referred to as "NOEt-P-Asp(OMe)(I)].

In the same manner, NOEt-P-Me(II) is converted to 2-hydroxy-3-ethoxyiminoethiliden-protoporphyrin [hereinafter referred to as "NOEt-P-Asp(OMe)(II)].

NOEt-P-Asp(OMe)(I) or NOEt-P-Asp(OMe)(II) thus obtained is hydrolyzed by, for example, sodium hydroxide after dissolved and suspended in, for example, ethanol, thus sodium salts of the porphyrin compounds of the present invention represented by formula (I) or formula (II) is obtained.

Free carboxylic acid of the porphyrin compound is derived from treating these sodium salts with weak acid.

Accordingly, compounds stated below are provided as porphyrin compounds of the present invention.
(1) 13,17-bis[(1,2-dicarboxylethyl)carbamoylethyl]-3-ethenyl-7-hydroxy-8-ethoxyiminoethylidene-2,7,12,18-tetramethyl-porphyrin [hereinafter referred to as "NOEt-P-Asp(I)" ],
(2) 13,17-bis[(1,2-dicarboxyethyl)carbamoylethyl]-8-ethenyl-2-hydroxy-3-etoxyiminoethylidene-2,17,12,18-tetramethyl-porphyrin (hereinafter referred to as "NOEt-P-Asp(II)").

The porphyrin compound provided by the present invention is used for a photodynamic diagnosis and/or treatment of animals. Formulation of the compound is done according to the common method to the ones skilled in the art. When the porphyrin compound of the present invention is free acid, the object agent is formulated by dissolving it in suitable buffer, whereas in the case the porphyrin compound of the present invention is sodium salt, the object agent is formulated by dissolving it in physiological saline. Examples of suitable additives to be used are pharmaceutically acceptable adjuvant such as organic solvent, pH adjuster such as acid, base and buffer, stabilizer such as ascorbic acid, excipient such as glucose and isotonic agent such as sodium chloride.

The porphyrin compound of the present invention possesses features of photosensitizer for PDT such as long phosphorescence life, remarkable accumulability to specific internal organ, especially to cancer locus, good cell killing effect when exposed to light as determined by a dancyl methionine test, excellent absorption wavelength, water solubility and purity.

The good water solubility of this compound enables a preparation of a high concentration solution such as 50 mg/ml. Furthermore, the compound exhibits a high stability in vivo, as well as in vitro. When used for photodynamic diagnosis and/or treatment of animals as photosensitizer for PDT in general, it is desirable to administer the compound to a subject in a dose of 1–10 mg/kg body weight.

As discussed above, the porphyrin compound of the present invention is structurally characterized in that it has an amino acid residue, especially aspartic acid residue, and further ethoxylimino group, and as result, it exhibits various physiological and pharmacological properties.

As one of the properties, the compound selectively accumulates in tumor cells and is excreted therefrom at a slow rate. On the other hand, excretion from normal organs and cells is rapid and therefore it does not damage such organs and cells, and does not cause phototoxicity.

Furthermore, according to the present invention, the conversion of a porphyrin into a chlorin derivative allows the absorption wavelength to shift to infrared region and, as a result, it becomes possible to attain therapeutic efficacy for cancers in deep site. Accordingly, the porphyrin derivative of the present invention is highly useful as a photosensitizer for PDT for cancers and malignant tumors in animals.

EXAMPLES

The present invention will be described in more detail by referring to the following examples.

Example 1

Synthesis of Mixture of 7-hydroxy-8-oxoethylidene-protoporphyrin Dimethylester [P-Me(I)] and 2-hydroxy-3-oxoethylidene-proto-porphyrin Dimethyl Ester [P-Me(II)], Position Isomer of P-Me(I)

The title compounds were synthesized by the method of P. K. Dinello et al., ("*The porphyrins*", academic press, Vol. 1, 303(1978)). 100 g of protoporphyrin dimethyl ester (pp-Me) was dissolved in 10 L of chloroform. The resultant reaction mixture was allowed to react for one week under irradiation with light, thereby obtaining a mixture of chlorin derivatives of the porphyrin. After completion of the reaction, the reaction solution was concentrated under reduced pressure to give the residue (100 g) containing the title compounds in the mixture form.

Example 2

Isolation of P-Me(I) and P-Me(II) from Resultant Mixture

The resultant mixture obtained in Example 1 was dissolved in a mixture solution of dichloromethane-hexane, and the mixture solution was subjected to silica gel chromatography to eliminate insoluble matter, then the filtrate was concentrated. The resultant residue was treated with ethyl acetate, and obtained solid was recrystallized with pyridine-dichloromethane to give 7-hydroxy-8-oxoethylidene-protoporphyrin dimethylester [P-Me(I)]. Further, 2-hydroxy-3-oxoethylidene-protoporphyrin dimethylester [P-Me(II)], position isomer of P-Me(I), was obtained from the recrystallized filtrate.

Example 3
O-ethylimination and Hydrolysis of P-Me(I) and P-Me(II)

Each of P-Me(I) and P-Me(II) obtained in Example 2 was separately weighed out (10 g each) and dissolved in pyridine (190 ml) respectively. To the resultant solution was added 3 g of O-ethylhydroxylamine hydrochloride and allowed to react at 50° C. for 1.5 hours under stirring. After the reaction was completed, the reaction solution was poured into water to precipitate a crystalline substance. The crystalline substance was collected by filtration. In this manner, O-ethylimino P-Me(I) [NOEt-P-Me(I)] and O-ethylimino P-Me(II) [NOEt-P-Me(II)] were obtained (yield: quantitative).

Each of NOEt-P-Me(I) and NOEt-P-Me(II) obtained in the above procedure was dissolved in pyridine (260 ml) separately. The resultant solution was hydrolyzed with 1N sodium hydroxide solution in a conventional manner, and the reaction solution was neutralized, thereby giving a precipitate. The precipitate thus obtained was collected by filtration, washed and dried, and further purified with ethyl acetate-hexane mixture solution to give NOEt-P(I) and NOEt-P(II) (yield: quantitative).

Example 4
Conversion of NOEt-P(I) and NOEt-P(II) into Aspartic Acid Derivatives Thereof (a) Each of NOEt-P(I) and NOEt-P(II) obtained in Example 3 was separately weighed out (2 g each), dissolved in tetrahydrofuran, and converted into a dicyclohexylamine (DCHA) salt (2.0 g each) with DCHA in a conventional manner, respectively.

(b) Each of the resultant DCHA salts was dissolved in dimethylformamide. To the resultant solution was added aspartic acid dimethyl ester (AspOMe$_2$) hydrochloride and further added water soluble carbodimide (WSC). Each of the resultant solutions was allowed to react. After confirming the completion of the reaction by TLC, water was added to each reaction solution to thereby cause precipitation. Each resultant precipitate was washed with water, dried and dissolved in acetone/ethyl acetate mixture solution. The resultant mixture solution was, then purified by silica gel chromatography, and recrystallized to obtain NOEt-P-Asp(OMe)(I) and NOEt-P-Asp(OMe)(II) as dark greenish brown crystals.

Example 5
Production of NOEt-P-Asp(I) and NOEt-P-Asp(II)

Each of NOEt-P-Asp(OMe)(I) and NOEt-P-Asp(OMe)(II) obtained in Example 4 was separately weighed out (1 g each) and hydrolyzed in a conventional manner by dissolving them in ethanol and then 1N sodium hydroxide. After the reaction was completed (The reaction end point was confirmed by TLC.), ethanol was added to each reaction solution to thereby cause precipitation. Each resultant precipitate was collected by filtration and dissolved in water. To each resultant solution was added additional ethanol to thereby cause precipitation for further purification. In this manner, a sodium salt of NOEt-P-Asp(I) was obtained from NOEt-P-Asp(OMe)(I), and a sodium salt of NOEt-P-Asp(II) was obtained from NOEt-P-Asp(OMe)(II). MS:955 (M$^+$)

The infrared absorption spectrum of the sodium salt of NOEt-P-Asp(I) is shown in FIG. 1.

Example 6
Evaluation on Tissue Accumulability

Figure 2:
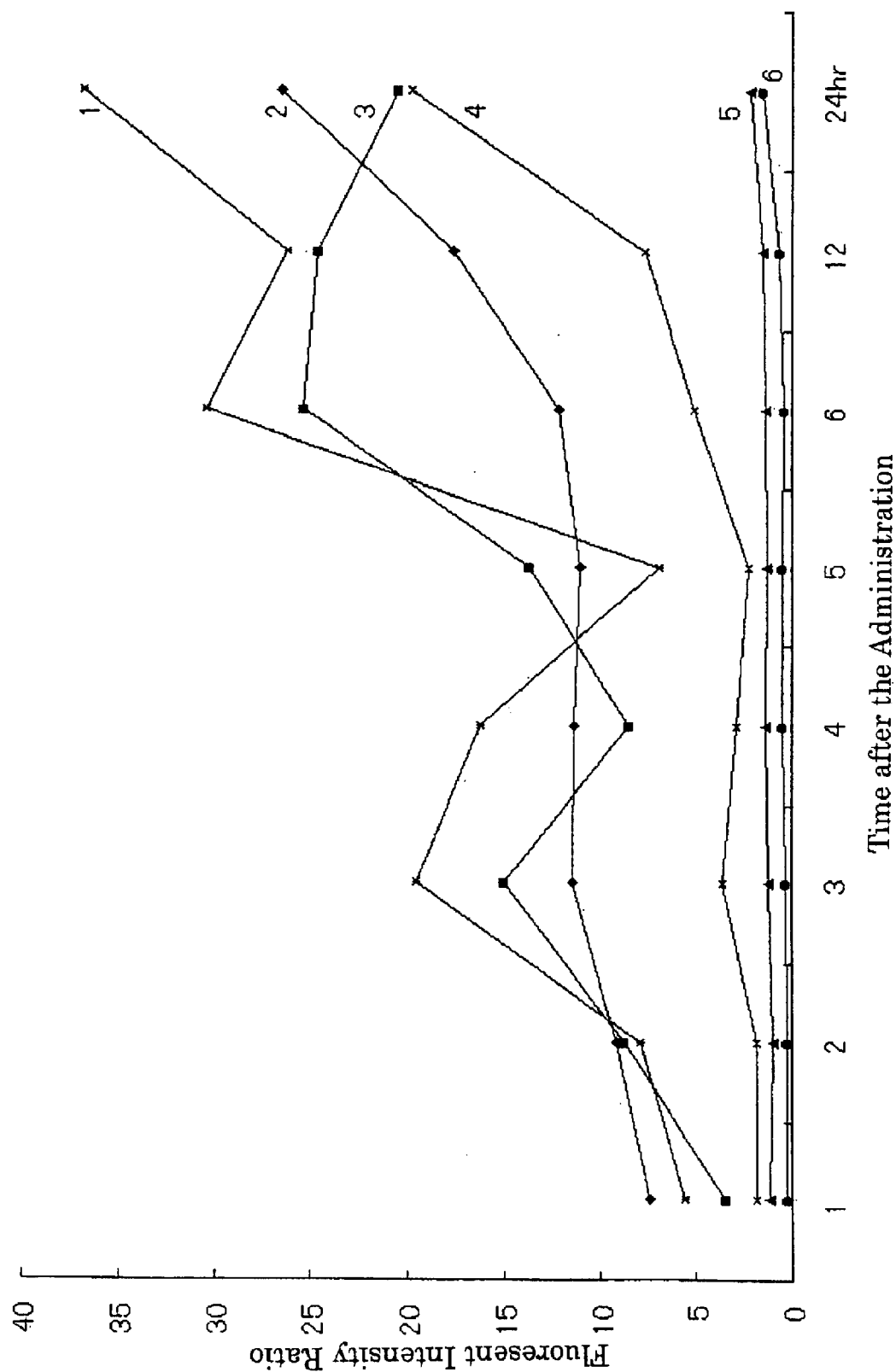
FIG. 2 shows the results of the accumulability to cancerous tissues (cancer/organ concentration) of the porphyrin compound of the formula (I) (NOEt-P-Asp). In the graph, the curve No.1 represents the result of cancer/brain, the curve No.2 represents the result of cancer/liver, the curve No.3 represents the result of cancer/lung, the curve No.4 represents cancer/muscle, the curve No.5 represents cancer/kidney, and the curve No.6 represents cancer/plasma.

3H/He mice (5 per group) implanted with tumor tissues of colon cancer Colon 26 for 14 to 21 days, were given an intravenous injection of sodium salt of each of NOEt-P-Asp(I) (10 mg/kg for each mouse) which had been diluted with a distilled water for injection. The blood samples were collected and the organs bearing the tumor tissue were extirpated after the injection, irradiated with N$_2$-pulsed laser (N$_2$, wavelength: 337 nm, 2 ns, 400–1,000 nm), and the excited fluorescent spectrum was measured. The wavelength in the range of 600 to 900 nm was examined based on the peak wavelength of NADH at 470 nm (determination of the distribution of the test compound in the organ by the surface fluorescence method using N$_2$-pulsed laser spectrophotometry). That is, the distributed concentration of sodium salt of NOEt-P-Asp(I) in cancer/organ (or plasma) ratio was determined by calculating the peak wavelength at 670 nm when the peak wavelength at 470 nm was considered as the basic value, 1. The result obtained after administration 1 to 24 hours is shown in FIG. 2. The sodium salt of NOEt-P-Asp(I) was found to have much higher accumulability to cancerous tissues.

Example 7
Evaluation on Photosensitizing Oxidation Reaction Using Dansyl Methionine To 1 ml of chloroform, 10 $\mu$M of Dansyl methionine, a substrate, was added, and then 0.1 $\mu$M of the photosensitizer of the present invention [sodium salt of NOEt-P-Asp(I)] was further added. Laser irradiation was conducted using Cold Spot PICL-SX (Nippon P.I. Co., Ltd.) which is halogen lamp, has 150 W wave length and 80,00 Lux, under stirring. The reaction solution was spotted at every minute on TLC plate (Kieselgel 60F254), and developed with chloroform methanol (3:2), then Dansyl methionine and its oxide (Dansylmethionine sulfoxide) were confirmed using UV lamp (254 nm). The time that Dansylmethionine disappeared completely on TLC plate was stated as the end of the reaction time, and photo oxidation reaction of photosensitizer was compared.

Photofrin II (Trade Mark) was used as a control of photosensitizer of present invention.

The result was shown in Table 1 below. The values in the table show the reaction end time in minutes, thus it shows that the smaller values (minutes) is, stronger the photosensitizing reaction.

As clearly shown in the table, photosensitizing agent of the present invention shows stronger photosensitivity reaction compared with Photofrin II (Trade Mark).

TABLE 1

| Name of the Compound | Degree of Photo Reaction |
| --- | --- |
| Photofrin II | 10> |
| NOEt-P-Asp(I) Na salt | 4 |
| NOEt-P-Asp(II) Na salt | 4 |

INDUSTRIAL APPLICABILITY

The porphyrin compound of the present invention has a high accumulability to cancerous cells, reactivity to external energy and a cancerous cell destroying effect. Furthermore, it exhibits no toxicity against normal cells. Accordingly, it is extremely useful as a diagnostic and therapeutic agent for cancer for animals.

What is claimed is:

1. A porphyrin compound represented by the following formula (I):

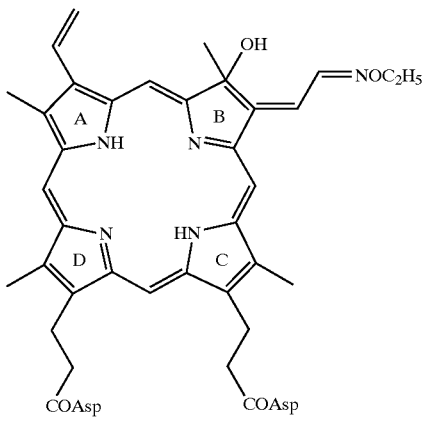

(I)

wherein Asp represents a residue of aspartic acid, or a pharmaceutically acceptable salt thereof.

2. A composition for use as a photodynamic diagnostic or therapeutic agent on cancers for animals comprising a diagnostic or therapeutic effective amount of the porphyrin compound of formula (I) or a pharmaceutically acceptable salt thereof according to claim 1 as an active ingredient.

3. A method of photodynamic diagnosis and/or treatment on cancers for animals comprising administering the composition of claim 2.

4. A porphyrin compound represented by the following formula (II):

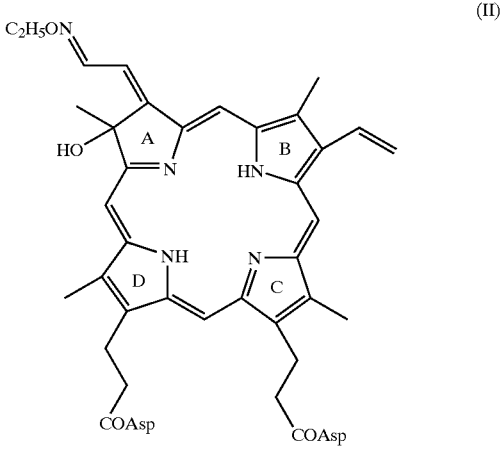

(II)

wherein Asp represents a residue of aspartic acid, or a pharmaceutically acceptable salt thereof.

5. A composition for use as a photodynamic diagnostic therapeutic agent on cancers for animals comprising a diagnostic or therapeutic effective amount of the porphyrin compound of formula (II) or a pharmaceutically acceptable salt thereof according to claim 4 an active ingredient.

6. A method of photodynamic diagnosis and/or treatment on cancers for animals comprising administering the composition of claim 4.

* * * * *